(12) United States Patent
Basset et al.

(10) Patent No.: US 6,281,160 B1
(45) Date of Patent: Aug. 28, 2001

(54) PROCESS FOR PREPARING CATALYSTS FOR USE IN ORGANIC COMPOUND TRANSFORMATION REACTIONS

(75) Inventors: Jean-Marie Basset, Villeurbanne; Jean-Pierre Candy, Caluire; Blaise Didillon; Fabienne Le Peltier, both of Rueil Malmaison; Olivier Clause, Chatou; Fatima Bentahar, Villeurbanne, all of (FR)

(73) Assignee: Institute Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/182,658

(22) Filed: Oct. 30, 1998

(30) Foreign Application Priority Data

Oct. 31, 1997 (FR) .................................................. 97/13684

(51) Int. Cl.$^7$ ............................. B01J 23/40; B01J 23/54; B01J 23/56; B01J 23/58; B01J 23/42

(52) U.S. Cl. ......................... 502/332; 502/325; 502/330; 502/333; 502/334; 502/339; 502/340; 502/224; 502/226; 502/227; 502/229; 502/230; 502/216; 502/222; 502/223

(58) Field of Search .................................... 502/325, 332, 502/333, 334, 339, 330, 340, 224, 226, 227, 229, 230, 216, 222, 223

(56) References Cited

U.S. PATENT DOCUMENTS

| | | | |
|---|---|---|---|
| 2,426,604 * | 9/1947 | Ferel ..................... | 585/259 |
| 3,200,167 * | 8/1965 | Reich ..................... | 585/260 |
| 3,297,776 * | 1/1967 | Reich et al. ........... | 585/262 |
| 3,531,543 * | 9/1970 | Clippenger et al. .... | 502/330 |
| 3,669,875 * | 6/1972 | Plank et al. ............ | 208/65 |
| 3,830,726 * | 8/1974 | Weisang et al. ....... | 208/138 |
| 3,929,683 * | 12/1975 | Antos .................... | 208/138 |
| 3,992,468 * | 11/1976 | Cosyns et al. ......... | 585/489 |
| 3,998,900 * | 12/1976 | Wihelm .................. | 502/227 |
| 4,409,410 * | 10/1983 | Cosyns et al. ......... | 585/259 |
| 4,507,401 * | 3/1985 | Dubois et al. ......... | 502/242 |
| 4,513,098 * | 4/1985 | Tsao ..................... | 502/216 |
| 4,548,918 | 10/1985 | Bournonville et al. . | 502/154 |
| 4,645,752 | 2/1987 | Defresne et al. ...... | 502/66 |
| 4,658,080 * | 4/1987 | McFarland .............. | 585/260 |
| 4,691,070 * | 9/1987 | Nakamura et al. ..... | 585/259 |
| 4,727,216 * | 2/1988 | Miller .................... | 585/660 |
| 4,737,262 * | 4/1988 | Franck et al. .......... | 208/65 |
| 5,417,844 * | 5/1995 | Boitaux ................. | 585/260 |
| 5,446,230 * | 8/1995 | Travers et al. ......... | 585/748 |
| 5,456,822 * | 10/1995 | Marcilly et al. ....... | 208/136 |
| 5,510,550 * | 4/1996 | Cheung et al. ........ | 585/259 |
| 5,677,260 * | 10/1997 | Dongara et al. ....... | 502/339 |
| 5,679,241 * | 10/1997 | Stanley ................. | 585/262 |
| 5,719,097 * | 2/1998 | Chang et al. .......... | 502/325 |
| 5,877,369 * | 3/1999 | Wu et al. ............... | 585/419 |

FOREIGN PATENT DOCUMENTS 0 623 384   11/1994 (EP) .
2 594 711   8/1987 (FR) .

* cited by examiner

*Primary Examiner*—Elizabeth D. Wood
(74) *Attorney, Agent, or Firm*—Millen, White, Zelano & Branigan, P.C.

(57) ABSTRACT

In a process for preparing a catalyst comprising at least one support, at least one metal from group VIII of the periodic table and at least one additional element M selected from the group formed by germanium, tin, lead, rhenium, gallium, indium and thallium, metal M is introduced in an aqueous solvent in the form of at least one organometalic compound comprising at least one carbon-M bond.

42 Claims, No Drawings

PROCESS FOR PREPARING CATALYSTS FOR USE IN ORGANIC COMPOUND TRANSFORMATION REACTIONS

FIELD OF THE INVENTION

The present invention relates to a novel process for preparing a catalyst comprising at least one support, at least one metal from group VIII of the periodic table, and at least one additional element M selected from germanium, tin, lead, rhenium, gallium, indium and thallium. The catalyst can also contain a further metal selected from the group formed by alkali or alkaline-earth metals and/or a metalloid such as sulphur and/or any other chemical element such as a halogen or a halogen-containing compound.

BACKGROUND OF THE INVENTION

Patents and publications demonstrating that the addition of promoters to a base metal improves the quality of catalysts exist in large numbers. Such elements are added in different forms such as mineral salts or organometallic compounds. In general, more active or more selective catalysts are obtained which are sometimes also more stable than the corresponding monometallic catalyst. The manner in which such modifying agents are introduced is not unimportant as it dictates the properties of the catalyst to a great extent.

Thus catalyst formulations used in hydrocarbon conversion processes have been the subject of a very large number of studies. Supported metallic catalysts have been described, in particular in U.S. Pat. No. 3,998,900 and French patent FR-A-2 495 605. They contain a metallic phase based on platinum, modified by an additional metal M such as tin, supported on refractory inorganic oxides such as alumina. Metal M is advantageously introduced using an organometallic compound of that metal M. Such a method of introducing metal M has already been described in patents U.S. Pat. No. 3,531,543 and U.S. Pat. No. 4,548,918.

The processes cited above describe the production of a catalyst using at least one organometallic compound of metal M. Metal M is introduced in the form of at least one organometallic compound selected from the group formed by complexes, in particular carbonyl or polyketone complexes of metals M, and metal hydrocarbyls of metal M such as alkyls, cycloalkyls, aryls, metal alkylaryls and metal arylalkyls.

Introducing the additional element M in the form of an organometallic compound leads to more effective catalysts but necessitates the use of an organic solvent. The impregnating solvent described in U.S. Pat. No. 4,548,918 is selected from the group formed by oxygen-containing solvents containing 2 to 8 carbon atoms per molecule, paraffin, naphthene or aromatic hydrocarbons essentially containing 6 to 15 carbon atoms per molecule, and halogen-containing oxygen-containing organic compounds containing 1 to 15 carbon atoms per molecule. Such solvents can be used alone or mixed together.

SUMMARY OF THE INVENTION

In the present invention we have discovered that particularly effective catalysts can be prepared by introducing metal M in the form of an organometallic complex which is soluble in an aqueous solvent. This represents a considerable advance as regards ease of use during production of the catalyst. Using industrial quantities of organic solvents has many disadvantages as regards safety (flammability, toxicity) and as regards costs.

The support for the catalyst of the invention comprises at least one refractory oxide which is generally selected from oxides of metals from groups IIA, IIIA, IIIB, IVA or IVB of the periodic table such as oxides of magnesium, aluminium, silicon, titanium, zirconium or thorium, used alone or mixed together or mixed with oxides of other elements from the periodic table. Charcoal can also be used. X, Y, mordenite, faujasite, ZSM-5, ZSM-4 or ZSM-8 type zeolites or molecular sieves can also be used, as well as mixtures of oxides of group IIA, IIIA, IIIB, IVA or IVB metals with a zeolitic material.

For hydrocarbon transformation reactions, alumina constitutes the preferred support, the specific surface area of which is advantageously in the range 5 to 400 $m^2$ per gram, preferably in the range 50 to 350 $m^2$ per gram. When transforming organic functions, silica, charcoal and alumina are the preferred supports.

In addition to a support, the catalyst of the invention includes:

a) at least one group VIII metal selected from iridium, nickel, palladium, platinum, rhodium and ruthenium. Platinum and palladium are preferred metals for hydrocarbon conversion reactions. Rhodium and ruthenium are preferred metals for transforming functional molecules. The percentage by weight is in the range 0.1% to 10%, preferably in the range 0.1% to 5%, for example.

b) at least one additional element M selected from the group formed by germanium, tin, lead, rhenium, gallium, indium and thallium. Tin and germanium are preferred elements. The percentage by weight is in the range 0.01% to 10%, preferably in the range 0.02% to 5%. In some cases, at least two of the metals from this group can advantageously be used at once.

Depending on the application, the catalyst can optionally also contain 0.1% to 3% by weight of a halogen or halogen-containing compound. It can also contain 0.1% to 3% by weight of an alkali or alkaline-earth metal. Optionally, it can also contain 0.01% to 2% by weight of an element such as sulphur.

The catalyst can be prepared using different procedures for impregnating the support and the invention is not limited to any specific impregnation procedure. When several solutions are used, intermediate drying and/or calcining steps can be carried out.

The additional element M can be introduced during production of the support. One method, for example, consists of blending the moist powdered support with catalyst precursors and then forming and drying.

The group VIII metal, additional metal M, optional halogen or halogen-containing compound, optional alkali or alkaline-earth metal, and optional metalloid, can be introduced simultaneously or successively, in any order. In accordance with the invention, the characteristic feature of contact with the organometallic element M is that it is introduced in an aqueous solvent.

In a further method, the additional metal M can be introduced during synthesis of the support using a sol-gel type technique. As an example, for a support containing alumina, a mixed metal M—alumina gel can be obtained by hydrolysing an organic solution of $Al(OR')_3$ in a solvent such as ROH or R'OH using an aqueous solution of an organometallic compound of metal M. R and R' represent a methyl, ethyl, isopropyl, n-propyl or butyl type alkyl group or a heavier group such as n-hexyl. The alcoholic solvent must be highly dehydrated before introducing the aluminium alcoholate. After hydrolysis, heat treatment of the gel obtained carried out at a temperature in the range 200° C. to 800° C., preferably in the range 300° C. to 700° C., and more preferably in the range 400° C. to 500° C., ensures complete reaction of the hydrosoluble organometallic compound of metal M with the gel, which causes formation of the mixed oxide $Al_2O_3$—$MO_x$.

In a still further method, metal M can be added to an alumina sol. U.S. Pat. No. 3 929 683 describes introducing tin in the form of a salt, for example $SnCl_2$, into an alumina sol. In the present invention, it is possible to add a hydrosoluble organometallic compound of metal M to an alumina hydrosol obtained, for example, by precipitating an acid solution of $AlCl_3$ at pH 4–5, then encouraging the compound of metal M to react with the alumina hydrosol, for example using heat or a base.

The precursor of element M can be selected from the group formed by halogen-containing compounds, hydroxides, oxides, carbonates and carboxylates of organometallic compounds of element M, this list not being limiting. These compounds comprise at least one carbon-M bond. As an example, the precursor of element M can be selected from trimethyl halides $Me_3MX$, dimethyl dihalides $Me_2MX_2$, trimethyl hydroxides $Me_3MOH$, dimethyl dihydroxides $Me_2M(OH)_2$, triethyl halides $Et_3MX$, diethyl dihalides $Et_2MX_2$, triethyl hydroxides $Et_3MOH$, isopropyl dihalides $iPr_2MX_2$, or bis-tributyl oxides $[Bu_3M]_2O$, where X represents a halogen. The precursor of element M can also be selected from compounds with general formula $(R_1)_xM(R_2)_y$ where x+y=the valency of metal M and where $R_1$ is selected from the group formed by alkyl, cycloalkyl, aryl, alkylaryl and arylalkyl functions, and $R_2$ is a function with formula $C_aH_bR'_c$, where R' represents a hydroxide, carboxylate, $PO_3H$ or $SO_3H$ function.

In one preferred preparation technique in accordance with the invention, the catalyst is obtained by impregnating the support using an aqueous or organic solution of at least one group VIII metal compound, the volume of the solution preferably being in excess with respect to the retention volume of the support or equal to that volume. The impregnated support is then filtered, optionally washed with distilled water then dried and calcined in air, normally between 110° C. and about 500° C., then reduced in hydrogen at a temperature which is normally in the range about 200° C. to about 600° C., preferably in the range about 300° C. to about 500° C. The product obtained is then impregnated with an aqueous solution of at least one compound of tin, germanium, lead, rhenium, gallium, indium or thallium. Particularly advantageously, an aqueous solution of a carboxylate compound of tin is used. The volume of the aqueous solution is preferably equal to the retention volume of the support, more preferably in excess with respect to that volume. The concentration of at least one metal M in the aqueous solution is advantageously in the range 0.01 to 25 mmol/l, preferably in the range 0.5 to 20 mmol/l, and more preferably in the range 0.5 to 15 mmol/l. The pH of the solution is advantageously between 10 and 14, preferably between 10 and 12.

After leaving the support impregnated with the group VIII metal in contact with the aqueous solution containing at least one compound of element M for several hours, the product is filtered, optionally washed with water, then dried. In this method, the operation is completed by reducing between 300° C. and 600° C., preferably in a stream of hydrogen for several hours. The operation can also be completed after the drying step by calcining between 300° C. and 600° C. in a stream of air.

In a further technique in accordance with the invention, the catalyst is obtained by impregnating with an aqueous solution of at least one compound of said metal M, the volume of the solution preferably being equal to the retention volume of the support, more preferably in excess with respect to that volume. Particularly advantageously, an aqueous solution of a tin carboxylate compound is used. The concentration of at least one metal M in the aqueous solution is advantageously in the range 0.01 to 25 mmol/l, preferably in the range 0.5 to 20 mmol/l, more preferably in the range 0.5 to 15 mmol/l. The pH of the solution is advantageously in the range 10 to 14, more preferably in the range 10 to 12. After leaving the solid and impregnating solution in contact for several hours, the product is then dried. The operation is normally completed by calcining between 300° C. and 600° C., preferably in a stream of air for several hours. The solid obtained is then impregnated using an aqueous or organic solution of at least one group VIII metal compound, the volume of the solution preferably being in excess with respect to the retention volume of the support or equal to that volume. After several hours of contact, the product obtained is dried and calcined in air between 300° C. and 600° C., preferably in a stream of air for several hours.

Before use, the catalyst is reduced in hydrogen, for example between 20° C. and 600° C., to obtain an active metal phase. This treatment consists, for example, in slowly raising the temperature in a stream of hydrogen to the maximum reduction temperature, in the range 20° C. to 600° C., for example, preferably in the range 90° C. to 500° C., followed by maintaining that temperature for a period of 1 to 6 hours, for example.

This reduction can be carried out immediately after calcining or later at the user's location. It is also possible to directly reduce the dried product at the user's location.

It is also possible to carry out prior reduction of the group VIII metal compound in solution using organic molecules with a reducing nature such as formic acid. The compound of additional element M can be introduced simultaneously or successively. The solid can then be directly used when the catalytic reaction requires an aqueous solvent, which is particularly suitable when transforming organic functions. A further possibility consists of filtering then drying the catalyst obtained. It can then be calcined followed by reduction using the conditions described above. It is also possible to carry out direct reduction of the dried product.

The catalyst prepared in accordance with the invention can be used in a hydrocarbon transformation processes used in the refining and petrochemicals field. It can also be used in processes used in the field of chemistry.

The following examples illustrate the invention without in any way limiting its scope.

EXAMPLE 1

Two catalysts A and B were prepared, each comprising 0.7% by weight of platinum and 0.15% by weight of tin. The support was a Degussa alumina with a specific surface area of 200 $m^2$ per gram.

Catalyst A (comparative)

The support was calcined at 500° C. in dry air for 5 hours then brought into contact with an ammoniacal solution (1 N) for 15 hours with nitrogen bubbled through. Platinum was deposited by introducing a solution of platinum tetramine hydroxide. The suspension was filtered, washed with distilled water and dried at 110° C. in a stream of nitrogen. 3 grams of the solid containing 0.7% by weight of platinum was then reduced in a stream of hydrogen for 4 hours at 450° C. The catalyst was placed in a reactor containing heptane, under hydrogen. Tetrabutyltin was injected at 20° C. After 24 hours of reaction at room temperature in a hydrogen atmosphere, the solid was filtered, washed with heptane then dried at 80° C. It was then reduced in a stream of hydrogen at 550° C. for 4 hours.

Catalyst B (in accordance with the invention)

Catalyst B was prepared from 3 grams of solid containing 0.7% by weight of platinum, reduced at 450° C. in a stream of hydrogen for 4 hours. The catalyst was then placed in a reactor under hydrogen containing 50 cm$^3$ of an aqueous ammoniacal solution (pH 11) containing 4.5 mg of tin in the form of tributyltin acetate ($Bu_3SnOC(O)CH_3$). After 24 hours of contact in a hydrogen atmosphere, the reaction mixture was filtered, washed, then dried at 80° C. IT was reduced in a stream of hydrogen at 550° C. for 4 hours.

Catalyst C (in accordance with the invention)

The support was prepared by hydrolysing a solution of aluminium isopropylate $Al(OiPr)_3$ in isopropanol using an aqueous solution of tributyltin acetate ($Bu_3SnOC(O)CH_3$), followed by heat treatment at 450° C. Platinum was then deposited by dry impregnating with hexachloroplatinic acid containing 0.7% by weight of platinum with respect to the calcined support. After calcining at 450° C. for 12 hours, the catalyst was reduced in a stream of hydrogen at 500° C. for 4 hours.

EXAMPLE 2

An isobutane dehydrogenation test was carried out on catalysts A, B and C in an isothermal tube reactor. 1 g of catalyst was reduced at 550° C. for 2 hours in a stream of 2 litres per hour of hydrogen. After injecting the feed, the temperature was stabilised at 550° C. The gaseous effluents were analysed on-line using gas chromatography.

The operating conditions were as follows:

| | |
|---|---|
| feed: | $iC_4$ N35 liquid air |
| temperature: | 550° C. |
| pressure: | 0.1 MPa |
| $H_2/iC_4$(molar): | 1 |
| hourly mass flow rate of liquid $iC_4$/mass of catalyst: | 725 h$^{-1}$ |

The results obtained under these conditions are shown in Table 1.

| Catalysts | Duration (h) | Activity (a) | Isobutene selectivity (b) |
|---|---|---|---|
| A | 1 | 20.0 | 99.1 |
| | 3 | 18.4 | 99.1 |
| | 5 | 17.6 | 99.3 |
| B | 1 | 25.0 | 99.2 |
| | 3 | 23.5 | 99.3 |
| | 5 | 23.0 | 99.3 |
| C | 1 | 22.1 | 99.1 |
| | 3 | 18.8 | 99.1 |
| | 5 | 17.8 | 99.3 |

(a) (moles. g Pt$^{-1}$.s$^{-1}$.10$^{-3}$)
(b) (mole %)

These results clearly show that the catalytic performances of catalysts B and C, prepared in accordance with the invention from an organometallic precursor of element M in an aqueous phase, were at least identical to and possibly better than those of catalyst A prepared from tetrabutyltin in an organic phase in accordance with the prior art.

What is claimed is:

1. In a process for preparing a catalyst comprising at least one support, at least one metal from group VIII of the periodic table and at least one additional element M selected from the group consisting of germanium, tin, lead, rhenium, gallium, indium and thallium, the improvement comprising introducing said metal M into the support as an aqueous solution, said metal M being in the form of a hydrosoluble organometallic compound containing at least one carbon-M bond.

2. A process according to claim 1, in which the catalyst further contains at least one alkali or alkaline-earth metal.

3. A process according to claim 1, in which the catalyst further contains sulfur.

4. A process according to claim 1, in which the catalyst further contains at least one halogen or halogen-containing compound.

5. A process according to claim 1, in which the group VIII metal is selected from iridium, nickel, palladium, platinum, rhodium and ruthenium.

6. A process according to claim 1, in which element M is germanium or tin.

7. A process according to claim 1, in which the organometallic compound containing at least one carbon-M bond is selected from the group consisting of hydroxides, halogen-containing compounds, carbonates and carboxylates of organic compounds of element M, compounds with general formula $(R_1)_xM(R_2)_y$ where x+y=the valency of metal M and where $R_1$ is selected from the group formed by alkyl, cycloalkyl, aryl, alkylaryl and arylalkyl functions, and $R_2$ is a function with formula $C_aH_bR'_c$, where R' represents a hydroxide, carboxylate, $PO_3H$ or $SO_3H$ function.

8. A process according to claim 6, in which the organometallic compound containing at least one carbon-M bond is selected from the group consisting of hydroxides of organic compounds of element M.

9. A process according to claim 6, in which the organometallic compound containing at least one carbon-M bond is selected from the group consisting of carboxylates of organic compounds of element M.

10. A process according to claim 6, in which the organometallic compound containing at least one carbon-M bond is selected from the group is tributyltin acetate.

11. A process according to claim 1, in which the group VIII metal, additional element M, optional halogen or halogen-containing compound, optional alkali or alkaline-earth metal, and optional sulfur are introduced into the support successively.

12. A process for preparing a catalyst according to claim 1, in which the following steps are carried out successively
   impregnating a support using an aqueous or organic solution of at least one group VIII metal, filtering, drying, calcining and reducing;
   impregnating the product obtained using an aqueous solution of at least one compound of additional element M, filtering, drying, optionally reducing, and calcining.

13. A process according to claim 1, in which the support is impregnated with an aqueous solution of at least one compound of metal M, the volume of the solution being at least equal to the retention volume of the support.

14. A process according to claim 1, in which the concentration of at least one metal M in the aqueous solution is in the range 0.01 to 25 mmol/l.

15. A process according to claim 14, in which the concentration of at least one metal M in the aqueous solvent in the range 0.5 to 20 mmol/l.

16. A process for preparing a catalyst according to claim 1, in which the pH of the aqueous solution of at least one compound of metal M is selected so as to be between 10 and 14.

17. A process for preparing a catalyst according to claim 1, in which additional element M is introduced during production of the support.

18. A process for preparing a catalyst according to claim 17, in which additional element M is introduced during synthesis of the support using a sol-gel type technique.

19. A process for preparing a catalyst according to claim 18, in which an aqueous solution of an organometallic compound of metal M is used to hydrolyze an organic solution of an alkoxy compound of a metal of the support in an alcoholic solvent, then heated to a temperature in the range 200° C. to 800° C.

20. A catalyst comprising at least one support, at least one support, at least one metal from group VIII of the periodic table and at least one additional element M selected from the group consisting of germanium, tin, lead, rhenium, gallium indium and thallium prepared by a process comprising impregnating the support with said element M by treatment in an aqueous solvent with at least one organometallic compound containing at least one carbon-M bond.

21. A process according to claim 5, wherein the group VIII metal is platinum or palladium.

22. A process according to claim 16, wherein the pH is between 10 and 12.

23. The catalyst of claim 20, in which the catalyst further contains at least one alkali or alkaline-earth metal.

24. The catalyst of claim 20, in which the catalyst further contains sulfur.

25. The catalyst of claim 20, in which the catalyst further contains at least one halogen-containing compound.

26. The catalyst of claim 20, in which the group VIII metal is iridium, nickel, palladium, platinum, rhodium or ruthenium.

27. The catalyst of claim 20, in which element M is germanium or tin.

28. The catalyst of claim 20, in which the organometallic compound containing at least one carbon-M bond is selected from the group consisting of hydroxides, halogen-containing compounds, carbonates and carboxylates of organic compound of element M, compounds of formula $(R_1)_xM(R_2)_y$ where x+y=the valency of metal M and where $R_1$ is selected from the group consisting of alkyl, cycloalkyl, aryl, alkylaryl and arylalkyl functions, and $R_2$ is a function with formula $C_aH_bR'_c$, where R' represents a hydroxide, carboxylate, $PO_3H$ or $SO_3H$ function.

29. The catalyst of claim 20, wherein the organometallic compound containing at least one carbon-M bond is tributyltin acetate.

30. The catalyst of claim 20, wherein the process for preparing the catalyst comprises:

a) impregnating a support using an aqueous or organic solution of at least one group VIII metal, filtering, drying, calcining and reducing;
b) impregnating the product obtained from a) using an aqueous solution of at least one compound of element M, filtering, drying, optionally reducing, and calcining.

31. The catalyst of claim 20, wherein the process for preparing the catalyst comprises impregnating the support with an aqueous solution of at least one compound of metal M, the volume of the solution being at least equal to the retention volume of the support.

32. The catalyst of claim 20, wherein in the process for preparing the catalyst the concentration of at least one metal M in the aqueous solvent is in the range 0.01 to 25 mmol/l.

33. The catalyst of claim 20, wherein in the process for preparing the catalyst the pH of the aqueous solvent of at least one compound of metal M is selected so as to be between 10 and 14.

34. The catalyst of claim 20, wherein in the process for preparing the catalyst element M is introduced during production of the support.

35. The catalyst of claim 20, wherein in the process for preparing the catalyst element M is introduced during synthesis of the support using a sol-gel type technique.

36. The catalyst of claim 20, wherein in the process for preparing the catalyst an aqueous solution of an organometallic compound of metal M is used to hydrolyze an organic solution of an alkoxy compound of a metal of the support in an alcoholic solvent, then heated to a temperature in the range 200° C. to 800° C.

37. A process according to claim 12, wherein the support is alumina, the group VIII metal is platinum, the aqueous solution of at least one compound of additional element M is an aqueous solution of tributyltin acetate having a pH of between 10 and 14 and the resultant product containing the additional element M is calcined and reduced.

38. A catalyst produced by the process of claim 37.

39. A process according to claim 1, wherein metal M is gallium, indium, thallium or rhenium.

40. A composition according to claim 20, wherein metal M is gallium, indium, thallium or rhenium.

41. A process according to claim 1, wherein said catalyst consists essentially of said at least one support, said at least one metal from group VIII of the periodic table and said at least one additional element M.

42. A process according to claim 1, wherein said catalyst consists of said at least one support, said at least one metal from group VIII of the periodic table and said at least one additional element M.

* * * * *